United States Patent [19]
Safford

[11] 3,955,576
[45] May 11, 1976

[54] TAPE FASTENER SYSTEM FOR DISPOSABLE DIAPERS

[75] Inventor: Robert D. Safford, Sao Paulo, Brazil

[73] Assignee: Kimberly-Clark Corporation, Neenah, Wis.

[22] Filed: Apr. 21, 1975

[21] Appl. No.: 569,879

[52] U.S. Cl. .............................. 128/287; 128/284
[51] Int. Cl.² ........................................ A61F 13/16
[58] Field of Search .............. 128/284, 287; 24/67, 24/73 VA

[56] References Cited
UNITED STATES PATENTS

| | | | |
|---|---|---|---|
| 3,257,677 | 6/1966 | Batchelder et al. | 128/284 |
| 3,848,594 | 11/1974 | Buell | 428/77 X |
| 3,869,761 | 3/1975 | Schaar | 128/284 X |

*Primary Examiner*—Aldrich F. Medbery
*Attorney, Agent, or Firm*—Daniel J. Hanlon, Jr.; William D. Herrick; Raymond J. Miller

[57] ABSTRACT

A tape fastener system for disposable diapers in which the tape is disposed on the liner, or front cover, of the diaper, and is of a unitary composite construction such that an integral surface portion of the tape acts as a releasable protective means for a pressure sensitive surface area of the composite tape. The fastener system comprises a composite tape formed from two connected strips of pressure sensitive sheet material longitudinally aligned and joined to each other at a narrow zone of overlap. The strips are overlapped with their adhesive surfaces in contact so that one end portion of the composite tape adjacent the overlap zone has its adhesive surface disposed on the face of the tape opposite from face of the tape on which the adhesive surface of the other end portion is disposed. When the tape is in position on the diaper, the adhesive surface of the first end portion of the composite tape is secured to a corner of the front cover of the diaper adjacent the diaper edge and the other or second end portion of the composite tape is folded transversely at the diaper edge and at the overlap to overlie the first end portion surface with the adhesive surface of the second end portion releasably adhered to the backside of the first end portion. The latter acts as a releasable protective means from which the second end portion can be stripped when the diaper is prepared for attachment to the child.

5 Claims, 6 Drawing Figures

TAPE FASTENER SYSTEM FOR DISPOSABLE DIAPERS

BACKGROUND OF THE INVENTION

Most disposable diapers now manufactured and sold are provided with a pressure sensitive tape strip at each of the corners adjacent one end of the diaper for securing the diaper together at the waist of the child in the diapering process. One end portion of such tape is commonly attached to the back side of the diaper while the pressure sensitive adhesive surface on the other free end portion is covered with a strippable release-coated protective sheet which is removed from the tape when the diaper is applied to the child. While the protective strip can be simply stripped off and discarded, doing so is inconvenient. Accordingly it is preferred that the strippable protective sheet be arranged in such a manner that it will remain attached to the diaper in some way after the pressure sensitive adhesive on the free end portion of the tape is uncovered when preparing the tape for its fastening function. While there are several ways in which the latter is accomplished, in each instance, it requires a separate piece of material or a complicated structure, both of which add undesirably to costs.

This invention is directed toward a tape fastening system in which the element or releasable protective means which performs the function of the protective covering sheet is an integral part of the tape itself. Accordingly, there is no need to design an intricate attachment means for a separate protective sheet.

SUMMARY OF THE INVENTION

This invention is directed to a simplified tape fastener system for use with disposable diapers of the type which comprises an absorbent core interposed between a fluid-pervious body-contacting cover sheet and a fluid-impervious backing sheet; in which the tape fastener is provided with a protective covering means for a pressure sensitive surface area of the tape; and in which the protective covering means is an integral part of the tape itself.

The tape fastener system is comprised of a composite tape formed from two strips of flexible sheet material coated with pressure sensitive adhesive on one surface and a release coating on the other surface. The two strips are longitudinally aligned and joined to each other at a narrow zone of overlap with the adhesive surfaces of the overlapped strips in contact in the zone of overlap to form a permanent bond. One end portion of the composite tape adjacent the overlap zone has its adhesive disposed on the face of the composite tape opposite from that face of the composite tape on which the adhesive of the other end portion is disposed. The first end portion of the composite tape is secured by its adhesive surface to the cover sheet of the diaper at one corner adjacent the diaper edge, and the second end portion of the tape when in its temporary stored condition is folded transversely at the diaper edge and at the overlap into an overlying position on top of the first end portion of the tape. The adhesive surface of the second end portion is releasably adhered to the release-coated surface of the first end portion which acts as a temporary protective means for the adhesive. When the diaper is to be used, the second end portion is merely stripped away from its temporary disposition over the first end portion into an extended position outboard of the diaper edge where it is in position for securing the diaper about the waist.

The above features and advantages of the invention will become apparent by reference to the following specification and accompanying drawings.

DETAILED DESCRIPTION OF THE DRAWINGS AND THE PREFERRED EMBODIMENT

In describing the details of the tape fastener system of the invention, it will be understood that the disposable diaper with which the tape fastener system is associated is of conventional construction. That is, the structural elements of the diaper generally comprise an absorbent core of absorbent fibers or other absorbent material interposed between a fluid-pervious cover of nonwoven material or the like on the body contacting side and a fluid-impervious backing sheet of thin plastic film or the like on the other side. A variety of edge structures may be utilized at the sides and ends of the diaper to maintain the elements in unitary assembly. In addition, the finished diapers may be provided with a variety of folding arrangements adapted to facilitate handling, packaging and eventual fitting on the child.

This invention is readily adapted for use with all such forms of disposable diapers. As indicated earlier, most tape fasteners for diapers are initially attached to the backing sheet, especially those in which the adhesive protecting sheet remains secured to the diaper after the adhesive is uncovered for use. Also in most cases, the protective sheet is usually affixed to the front cover portion of the diaper. In instances where the adhesive fastener is initially attached to the front cover instead of the backing sheet, no structures are known in which the protective sheet is an integral part of the tape which remains attached to the diaper and serves as the fastening means after the adhesive portion is uncovered. This invention is directed to diapers in which the tape is initially secured to the cover sheet, and in which the protective release means is an integral part of the tape which remains attached to the cover when the diaper is in use. Accordingly, since the tape fastener is initially secured to the fluid-pervious cover sheet it is preferred that for best performance such cover sheet have high tensile strength in the cross direction or be reinforced where the tape is secured thereto, although these preferred properties are not essential to the basic concept of the invention.

Figure 1:
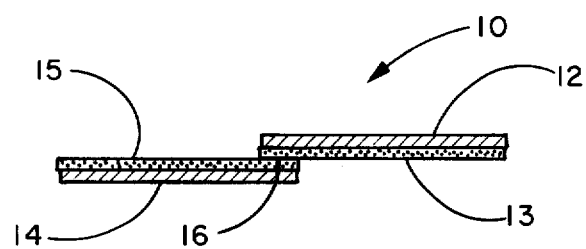
FIG. 1 is a side view in longitudinal section of the composite tape structure in accordance with the invention.

In the drawings, FIG. 1 illustrates, in a sectional side view, the construction of the composite tape used in the fastening system. As shown therein, composite tape 10 is comprised of two strips 12 and 14 of strong, flexible material such as resin- or latex-impregnated paper, plastic film, or cloth, coated on one surface with a pressure sensitive adhesive 13 and 15 and on the other surface with a release coating. For convenience, the two strips in the composite tape are further identified hereinafter as first end portion 12 and second end portion 14.

Pressure-sensitive tapes are usually provided with a release coating on the back side when supplied in roll form so that they can be unwound without difficulty during the manufacturing process, otherwise a separate slip sheet is required and the latter is prohibitively expensive for uses in this nature. Accordingly, it is assumed that the back side of the pressure-sensitive strips used in this invention are provided with the customary release coating.

First end portion 12 and second end portion 14 of the composite tape are overlapped at 16 with their respective pressure-sensitive adhesive surfaces 13 and 15 in adhering contact to provide a strong, permanent joint at the overlap 16.

In FIGS. 2, 2a, 3 and 3a, the composite tape of FIG. 1 is shown in both its operative and stored position and in association with the corner of a disposable diaper, illustrated in fragmentary form. As exemplified in the drawings, the disposable diaper is comprised of an absorbent core 20, a fluid permeable cover sheet 22, and a fluid-impermeable backing sheet 24 of thin plastic film. The cover sheet 22 is shown as being sealed directly to the backing sheet 24 at both the ends and edges of the diaper. Other suitable sealing means may be used in these areas without detracting from the invention described herein.

Figure 2:
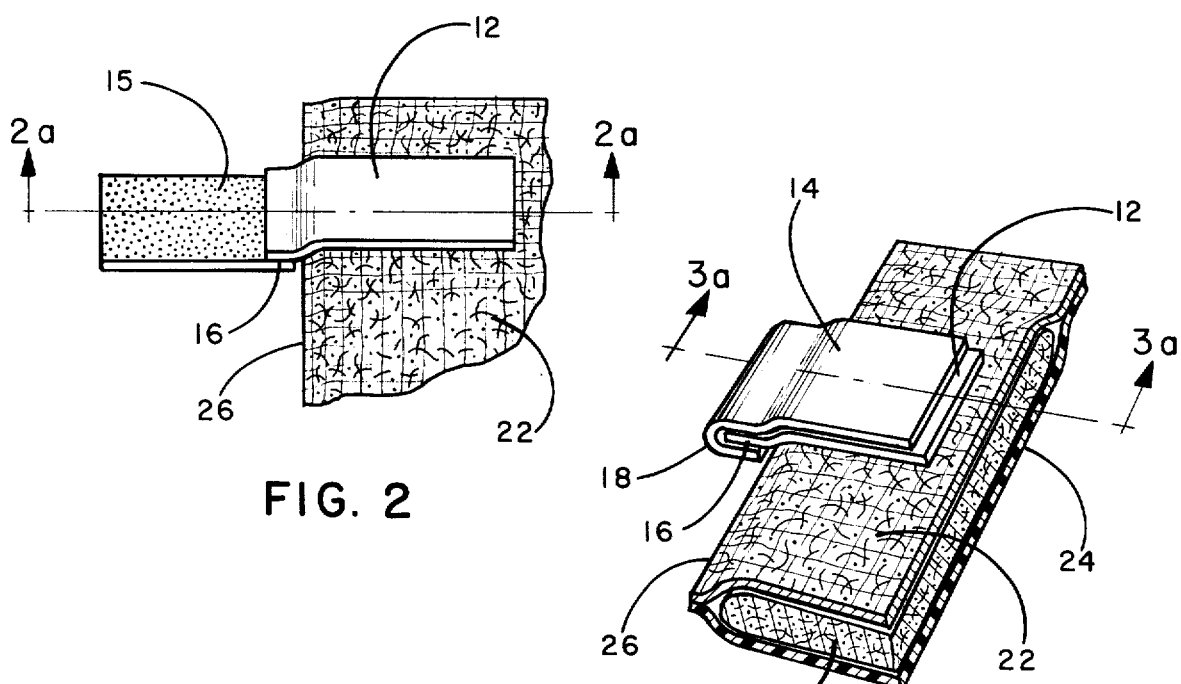
FIG. 2 is a fragmentary plan view of the corner portion of a disposable diaper with the composite tape structure of FIG. 1 shown in operative association therewith.
Figure 3:
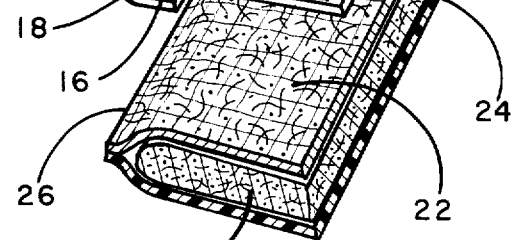
FIG. 3 is a perspective view of the corner fragment of a disposable diaper in which the composite tape of FIG. 1 is shown folded over on itself in its temporary storage or packaged position.
Figure 3A:
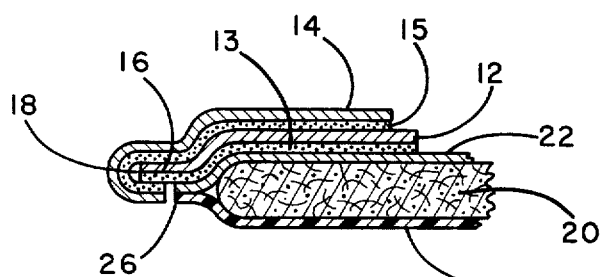
FIG. 3a is a section taken along line 3a—3a of FIG. 3.
Figure 2A:
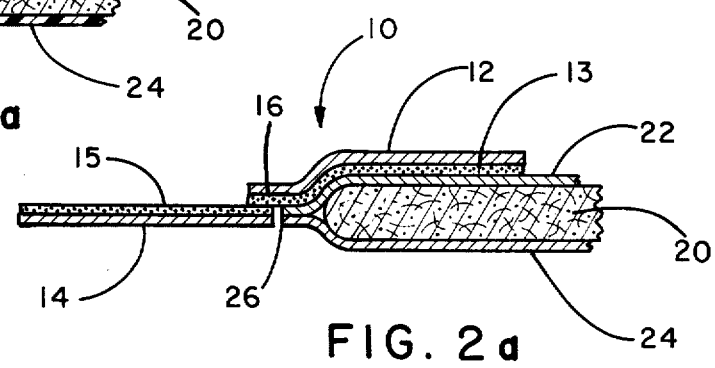
FIG. 2a is a section taken along line 2a—2a of FIG. 2.

In the preferred embodiment of the invention illustrated in the drawings, the first end portion 12 of composite tape 10 is secured to cover sheet 22 at one corner of the diaper by adhesive surface 13. Second end portion 14 and overlapping joint 16 extend beyond diaper edge 26. In FIGS. 2 and 2a, second end portion 14 is shown fully extended ready for use in fastening the diaper ends together. In FIGS. 3 and 3a, second end portion 14 is shown folded transversely on itself at the edge 18 of joint 16 to overlie first end portion 12 where it is held in releasable association with the back surface of first end portion 12 by adhesive surface 15. The back surface of first end portion 12 therefore acts as an integral releasable protective means for the second end portion 14. This is the packaged or storage position of the strip.

Figure 4:
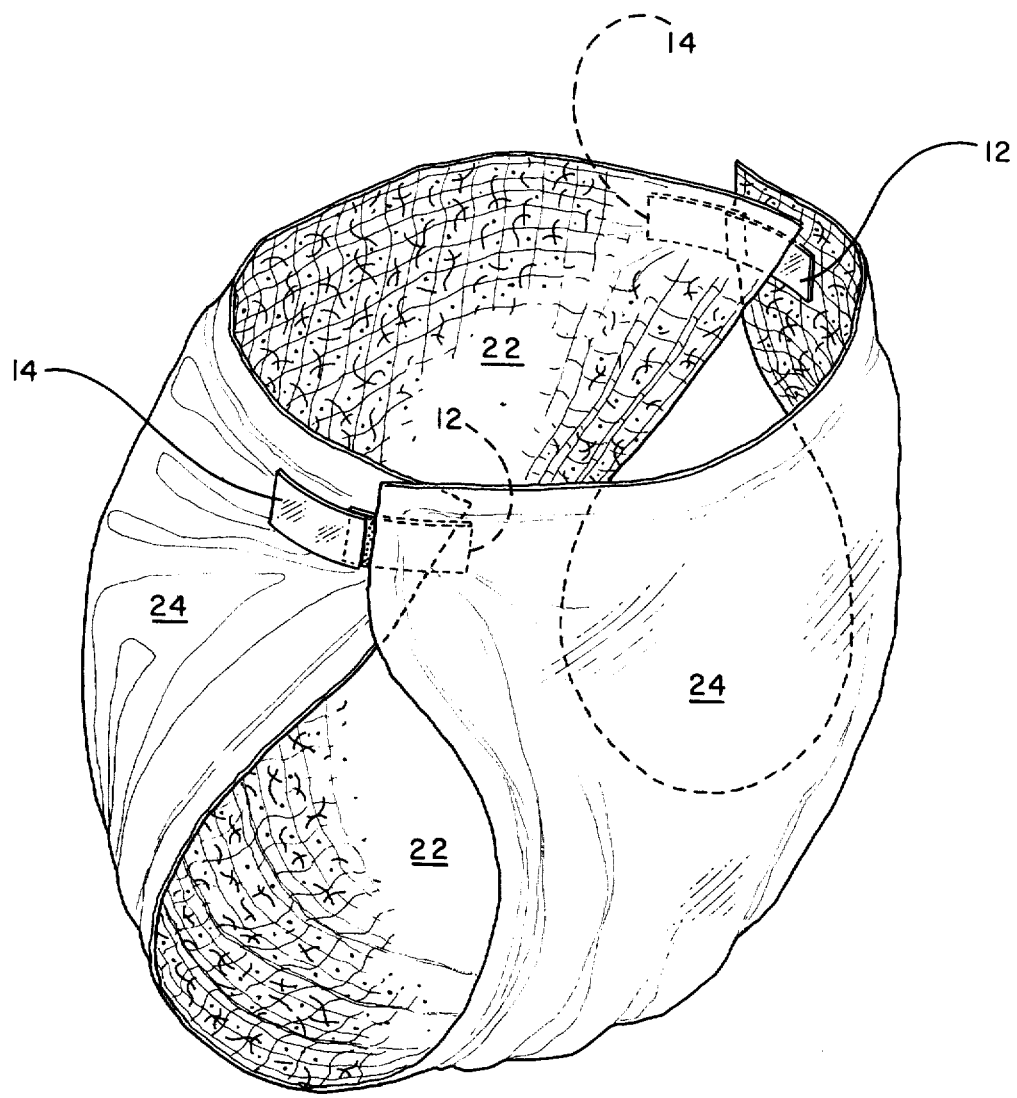
FIG. 4 is a perspective view of a disposable diaper as it appears when it is in position on a child, and with the tape fastening system of this invention in use to attach the overlapping ends of the diaper at the waist.

FIG. 4 illustrates a complete diaper and shows the tape fastening system as it appears in use when the diaper is fastened at the waist and is in position on the child. As shown therein, first end portion 12 of the composite tape remains secured to cover sheet 22 and second end portion 14 is secured to backing sheet 24 at a corner of the diaper on the opposite end of the diaper. Thus, it will be seen that, in accordance with the invention, the composite tape structure 10 serves the dual function of first storing the fastening end portion 14 in a temporary and protected non-operative position without the need of a separate protective sheet, and second, permitting end portion 14 to be conveniently extended to its operative position when needed for fastening purposes, without requiring the user to manipulate a separate protective sheet.

It should be noted here that prior to this invention it had been suggested that a unitary substrate in the form of a single strip might be used for the same purpose as described herein by coating half the length of one surface of a single strip with a pressure-sensitive adhesive while the other half length is provided with a pressure-sensitive adhesive on the opposite surface of the same strip. The reverse side of the strip in each of the respective adhesive-coated areas would then be coated with a suitable release coat. However, many difficulties are involved in providing such a structure. The first difficulty is that both the pressure-sensitive coating and the release coating must be applied with extreme precision on each surface in order that there is no overlap whatsoever, otherwise the adhesive would tend to peel off the substrate where it inadvertently overlaps the release coating on its side of the substrate. Second, when such a single piece tape is rolled up in the form needed for commercial operation, unless the tape is also rolled with such precision that the adhesive on one side does not contact the adhesive on the other side, great difficulty would be encountered in unrolling the tape. In other words, the tape would block in any overlapped areas. In any event, coating selected portions of a tape on reverse sides with the precision required is time consuming and results in excessive costs due to waste, numerous rewindings to obtain the desired precision, and the need for exact edge control during coating and rewinding. These production difficulties might be overcome by providing a separate continuous release sheet between convolutions of the roll, but the costs involved in providing such a separate interleaving sheet arrangement are prohibitive.

In addition to overcoming these difficulties, the separate strip construction of the composite tape of this invention can be varied in many ways, so that each of the separate strips which make up the composite tape may be tailored to meet specific adhesive requirements, e.g., by providing the first end portion with an adhesive which adheres more strongly to the nonwoven substrate which makes up the cover sheet, while the second end portion is compounded with an adhesive which adheres more firmly to plastic film or alternatively which adheres firmly to the plastic but which can be removed and then re-adhered if inspection or adjustment of the diaper is required. Other variations are also possible, one strip may be made of plastic while the other is a reinforced or impregnated paper. Innumerable combinations are possible.

The width of overlap is not critical as long as it provides a bond of sufficient strength to be permanent. An overlap of about one-fourth inch is preferred, although a width of from one-eighth to three-eighths inch is satisfactory.

In all of the drawings, the overlap portion of the composite tape is shown as being disposed outside of the diaper edge. It is understood of course, that this overlap portion may also be disposed over the cover sheet inboard of the diaper edge, so that when the composite tape is folded in its temporary storage position, none of the tape will extend beyond the diaper edge.

What is claimed is:

1. A tape fastener system in combination with a disposable diaper of the type which comprises an absorbent core interposed between a fluid-pervious body-contacting cover sheet and a fluid-impervious backing sheet, said tape fastener system comprised of a composite tape formed from two strips of flexible sheet material coated with pressure-sensitive adhesive on one surface and a release coating on the other surface, said strips being longitudinally aligned and joined to each other at a narrow zone of overlap with the adhesive surfaces of the overlapped strips being in contact at the zone of overlap to form a permanent bond, one end portion of the composite tape adjacent the overlap zone having its adhesive disposed on the face of the composite tape opposite from that face of the composite tape on which the adhesive of the other end portion is disposed, the first end portion of said composite tape being secured by said adhesive to the cover sheet of said diaper at one corner adjacent the diaper edge, and the second end portion of said composite tape being adapted to extend beyond the edge of the diaper for use in fastening the diaper around the waist.

2. The tape fastener system of claim 1 wherein the second end portion of said composite tape is folded transversely at the diaper edge into over-lying position over said first end portion with the adhesive face of said second end portion releasably adhered to the release coated surface of the first end portion.

3. The tape fastener system of claim 1 wherein said transverse fold is disposed at the edge of said overlap.

4. The tape fastener system of claim 3 wherein said transverse fold and the edge of said overlap are disposed outboard of the associated diaper edge.

5. The tape fastener system of claim 3 wherein said transverse fold and the edge of said overlap are disposed inboard of the associated diaper edge.

* * * * *

Notice of Adverse Decision in Interference

In Interference No. 100,041, involving Patent No. 3,955,576, R. D. Safford, TAPE FASTENER SYSTEM FOR DISPOSABLE DIAPERS, final judgment adverse to the patentee was rendered June 18, 1982, as to claims 1-5.
[*Official Gazette November 9, 1982.*]